United States Patent [19]

Herring

[11] Patent Number: 4,458,021

[45] Date of Patent: Jul. 3, 1984

[54] BLOOD GAS CONTROL

[75] Inventor: Kathryn D. Herring, Miami, Fla.

[73] Assignee: American Hospital Supply Corporation, Evanston, Ill.

[21] Appl. No.: 373,938

[22] Filed: May 3, 1982

[51] Int. Cl.³ .................. C09K 3/00; G01N 33/50; G01N 33/96

[52] U.S. Cl. .................................... 436/11; 435/2; 436/15; 436/16; 436/18; 422/41; 422/42; 422/43

[58] Field of Search ............... 436/11, 15, 16, 18; 435/2; 422/41, 42, 43

[56] References Cited

U.S. PATENT DOCUMENTS

| | | | |
|---|---|---|---|
| 3,466,249 | 9/1969 | Anderson | 436/11 |
| 3,859,049 | 1/1975 | Ware et al. | 436/11 |
| 4,001,142 | 1/1977 | Turner et al. | 436/11 |
| 4,116,336 | 9/1978 | Sorensen et al. | 436/11 |
| 4,151,108 | 4/1979 | Sorensen et al. | 436/11 |
| 4,163,734 | 8/1979 | Sorensen et al. | 436/11 |
| 4,183,962 | 1/1980 | Asher | 436/11 |
| 4,199,471 | 4/1980 | Louderback et al. | 436/11 |
| 4,279,775 | 7/1981 | Louderback et al. | 436/11 |
| 4,289,648 | 9/1981 | Hoskins et al. | 436/11 |
| 4,299,728 | 11/1981 | Cormier et al. | 436/11 |
| 4,397,392 | 8/1983 | Runck et al. | 436/11 |

*Primary Examiner*—Teddy S. Gron
*Attorney, Agent, or Firm*—John H. Faro

[57] ABSTRACT

Disclosed are cell-free, stable, aqueous blood gas controls containing a proteinaceous foaming agent. The addition of foaming agent to the blood gas control permits generation of a gas impermeable foam within the head space of a sealed ampule in which the control is packaged. Upon agitation of the ampule prior to opening, the foam thus generated effectively isolates the control fluid from the ambient environment, thereby maintaining the concentration of gases dissolved within the fluid at their assigned values.

9 Claims, 3 Drawing Figures

BLOOD GAS CONTROL

BACKGROUND OF THE INVENTION

1. Field of the Invention

This invention relates to a blood gas control. More specifically, this invention concerns itself with a cell-free, stable, aqueous blood gas control containing a proteinaceous foaming agent; and a method for protecting environmentally sensitive fluids from atmospheric contamination.

2. Description of the Prior Art

Improvements in instrumentation have made the determination of blood pH, partial pressure of oxygen and partial pressure of carbon dioxide relative routine procedures for diagnoses of medical problems. Since vigorous therapeutic treatment is often dictated by such test results, the accuracy of such tests is essential. Accordingly, the use of control materials to verify the reliability of instrumentation used in such analysis is critical and necessary to provide an immediate indication of unexpected analytical deviation by the automated test equipment.

In the past, such control materials were not readily available and had to be prepared by the medical technologist immediately prior to performing the subject test. Generally, this involved adding known quantities of oxygen and carbon dioxide gases to a Tonometer containing a control fluid sample at a fixed pH. Gases in the liquid are equilibrated within the Tonometer and the an aliquot portion thereafter removed by the technician for use as a control for the blood gas instrumentation. Prior to the development of commercially available controls, the performance of blood gas analysis could only be performed in specially equipped laboratories engaged in research in the blood gas field.

Even where such controls are available, they had limited shelf life and readily undergo changes in dissolved gas concentration upon their exposure to the atmosphere. Where such controls have contained proteinaceous material, the problem of potential bacterial contamination was ever present and could cause decrease in the levels of dissolved oxygen and increase of levels of carbon dioxide. U.S. Pat. No. 4,001,142 describes a blood gas control essentially free of protein. While the control described in the '142 patent does provide an adequate control function, it does significantly differ from human serum which has an endogenous level of protein in the range of 6-8 grams per deciliter.

Under ideal conditions, control materials used in the verification of instrumentation performance should have essentially the same constituents as those present in the fluid which is to be subjected to analysis. Thus, protein free blood gas controls, while minimizing the problems of bacterial contamination and abbreviated shelf life, are significantly less preferred than those control materials which more closely approximate the endogenous complement of fluid to be analyzed.

Accordingly, it is the object of this invention to remedy the above as well as related deficiencies in the prior art.

More specifically, it is the principle object of this invention to provide an aqueous blood gas control having an acceptable shelf life and yet which approximates the composition of human serum.

Another object of this invention is to provide an aqueous blood gas control which is both stable during storage and yet maintains the concentration of dissolved gases at essentially their assigned value upon exposure to the atmosphere.

Additional objects of this invention include providing a method for isolation of atmospherically sensitive fluids from atmospheric contamination through the provision of a gas impermeable foam between the atmospherically sensitive fluid and the ambient environment.

SUMMARY OF THE INVENTION

The above and related objects are achieved by providing an essentially cell-free, aqueous blood gas control for quality control measurement of blood pH and dissolved blood gases. The control is contained in a sealed receptacle which is impermeable to gas exchange between the control fluid and the ambient environment. In practice, the receptacle is only partially filled with the control fluid thereby providing a head space containing the same gases at the same assigned concentration as is present in the control fluid. The fluid also contans a proteinaceous foaming agent. The amount of proteinaceous foaming agent present in the fluid is insufficient to adversely affect the shelf life of the control and can approximate the concentration of protein in human serum. After brief agitation of the sealed receptacle containing the control fluid and the foaming agent, a foam is created which is impermeable to the transmission of gases of the type dissolved in the control fluid. Thus, upon opening the sealed receptacle, the foam effectively isolates the control fluid from the ambient environment thereby maintaining, for a finite interval, the level of dissolved gases in the fluid at essentially their assigned values. This invention also provides a method for protecting environmentally sensitive fluids, such as blood gas controls, from atmospheric contamination through the use of foaming agents, by generation of gas impermeable foams within the sealed receptacle containing the environmentally sensitive fluid prior to breaking of the seal and exposing the contents of the receptacle to the ambient environment.

DESCRIPTION OF THE INVENTION INCLUDING PREFERRED EMBODIMENTS

Figure 1:
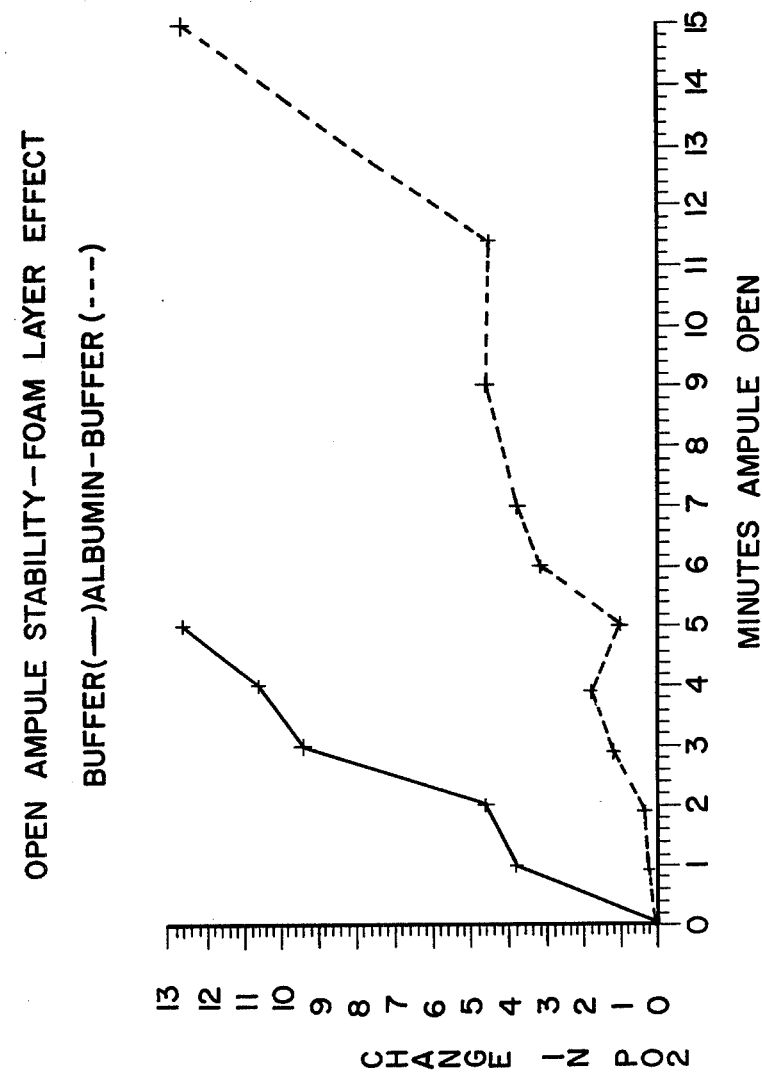
FIG. 1 is a graphical illustration of the relative stability of dissolved oxygen in a blood gas control containing the proteinaceous foaming agent and a blood gas control deficient in a proteinaceous foaming agent.
Figure 2:
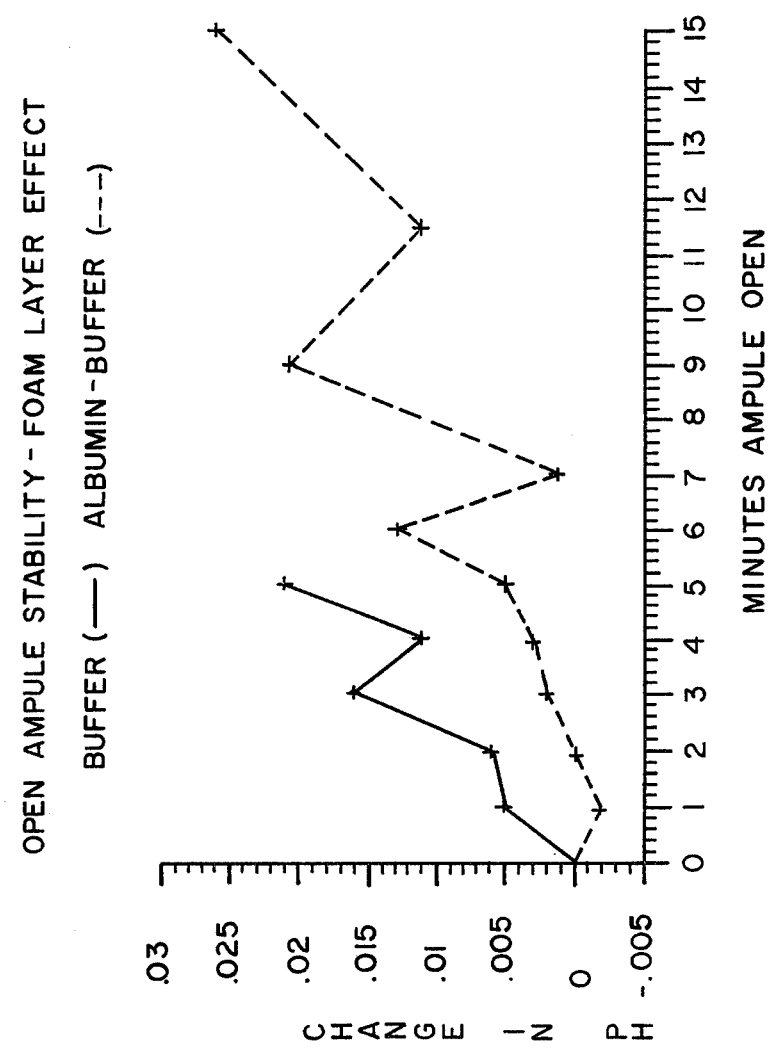
FIG. 2 is a graphical illustration of the relative stability of pH in a blood gas control containing a proteinaceous foaming agent and a blood gas control deficient in proteinaceous foaming agent.
Figure 3:
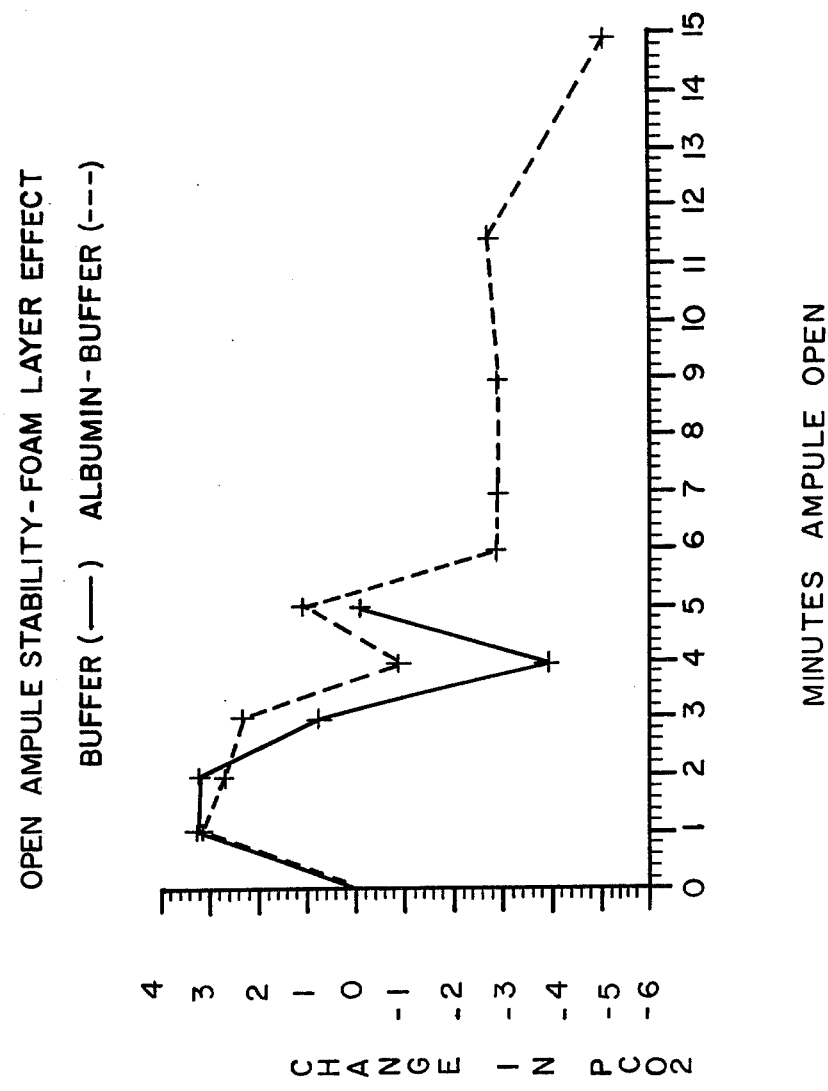
FIG. 3 is a graphical illustration of the relative stability of dissolved carbon dioxide in a blood gas control containing a proteinaceous foaming agent and a blood gas control deficient in proteinaceous foaming agent.

The blood gas controls of this invention are prepared by conventional manufacturing techniques using readily available materials. A typical control within the contemplation of this invention is prepared by simply combining, in the appropriate relative proportions, buffer, proteinaceous foaming agent and other standard auxiliary reagents and chemicals; the pH and concentration of dissolved carbon dioxide thereof being adjusted to the appropriate value (depending upon the nature of the control); an aliquot thereof placed in a sealable receptacle; the receptacle flushed with gas; and the receptacle sealed so as to create a head space above control fluid which is occupied by the gas.

The buffer selected for use in the preparation of these controls is preferably a phosphate-carbonate buffer system or a phosphate-TAPSO-carbonate buffer of the type described in U.S. Pat. No. 4,169,950. For example, in one preferred embodiment of this invention, the aqueous solution is buffered with 3-[N-Tris(hydroxylmethyl)methylamino]-2-hydroxypropane sulfonic acid (hereinafter "TAPSO"). TAPSO Buffer is described in U.S. Pat. No. 4,169,950 and can be obtained commercially from Research Organics, Inc., of Cleveland, Ohio. The pH of the buffer is adjusted within the limits prescribed for these controls by the addition of hydrochloric acid, sodium hydroxide and sodium bicarbonate in the appropriate amounts. For example, where a blood gas control is to have a relatively high level of dissolved carbon dioxide and a relatively low level of dissolved oxygen, the pH of the control must be relatively low (approximately pH 7.1). Conversely, where the blood gas control is to have a relatively low level of dissolved carbon dioxide and a relatively high level of dissolved oxygen, the pH of the control should be approximately 7.5. Other suitable buffers which can be used in these controls include sodium phosphate dibasic anhydride. The pH of this buffer can also be adjusted by the addition of appropriate quantities of hydrochloric acid, sodium hydroxide and sodium bicarbonate. The relative concentration of the buffer in the control can range from about 0.1 to about 2.0 moles per liter, with about 0.1 mole per liter being preferred. While the above buffers have proven suitable in this regard, other physiologically acceptable buffers having a pK of approximately 7.4 at 37° C. would also be acceptable for use in these controls providing their pH could be adjusted to within the range of application of these controls.

The foaming agent suitable for use in this control is a proteinaceous material, preferably a non-primate proteinaceous material, which when combined with the buffer in the appropriate relative concentration, is capable of generating an effective barrier against atmospheric contamination of the control fluid. The relative concentration of proteinaceous material which can be present in the control can approximate the amount of proteinaceous material generally found in human blood serum. Typically, human blood contains approximately 6 grams per deciliter proteinaceous materials. The concentration of proteinaceous materials in these controls should preferably approximate the amount present in human serum; however, lesser or greater amounts thereof may be employed depending upon the extent of foam desired within a control. In the event lesser quantities of protein are used, the viscosity of the control can be adjusted to approximate that of serum through simple addition of a thickener, such as polyethylene glycol.

The relative concentration of foaming agent in the control can range from about 5 to about 7 grams per deciliter and is preferably maintained at from about 5.5 to about 6.5 grams per deciliter in order to minimize the problems associated with shelf life stability of the control.

In addition to the proteinaceous constituent, the foaming agent can also comprise minor amounts of other foam generating substances, such as inert detergents. Of course, such detergents would have to be otherwise compatible with the control's essential characteristics; namely, not adversely alter the solubility of gases in the solution, result in denaturation of the protein present therein or adversely effect viscosity. In addition, such detergent should itself be independently capable of generating foam and/or extending the life time of the foam generated by the protein. A detergent which is suitable for use in this regard is Triton X-100 (available from Fisher Scientific Products).

In addition to the foregoing essential components, such blood gas controls can also contain standard auxiliary and complementary components such as preservatives and dyes.

Subsequent to preparation of blood gas control fluids having the foregoing essential and optional ingredients, the fluid is dispensed into sealable receptacles or vials. The amount of fluid relative to the volume of the vial is adjusted to allow for a head space of a pre-determined volume. The head space above the fluid is flushed with a gas prior to sealing so as to insure an environment in the vial which approximates the assigned values for the dissolved gases in the control fluid. The composition of the gas in the head space of the sealed vial will typically contain nitrogen, oxygen and carbon dioxide. The relative concentration of each gas in the control fluid is determined by the function the control is intended to serve. Typically, the dissolved gas concentration of nitrogen in such controls can range from about 80 to 90 percent; from about 2 to 20 percent for oxygen; and, from about 2 to 10 percent for carbon dioxide. As is readily appreciated, the concentration of the dissolved gases most frequently used in blood gas controls differs from the levels these gases are present in the ambient environment. Thus, in the absence of an effective means for isolation of the control fluid from the environment, the assigned values of such dissolved gases undergoes an almost immediate shift until the partial pressure of the dissolved gas establishes an equilibrium with the environment immediately above the surface of the fluid. The foam layer formed on the surface of the controls of this invention effectively delays the onset and establishment of such equilibrium and thus extends the useful period for dispensing the control fluid into the analytical instrument.

As noted hereinabove, the principle of generation of a foam barrier for prevention of atmospheric contamination of blood gas controls is also equally applicable to other solutions where it is either desirable or necessary to erect a barrier between an atmospherically sensitive solution and the environment. The nature of this foam barrier is unique in that it is possible to obtain access to the atmospherically sensitive solution upon opening of the sealed container without exposing the solution to environmental contact, such as in the case of septum vials.

The Examples which follow further illustrate the preparation and evaluation of blood gas controls of this invention and their comparison to controls lacking in foaming agent. Apparatus used in both the preparation and evaluation of these controls are standard or as hereinbefore specified. Parts and percentages appearing in such Examples are by weight unless otherwise indicated.

EXAMPLE I

A pair of blood gas controls are prepared, one containing foaming agent and one deficient in foaming using comparable reagents and techniques for the purpose of comparison of the relative stability of each upon exposure to atmospheric conditions. The stock solutions used in their preparation are set forth below:

| | |
|---|---|
| Acid: | 5 N HCl |
| Base: | 4 N NaOH |
| Source of $CO_2$: | 1 M $NaHCO_3$ |
| Phosphate Buffer: | 7.1 grams $Na_2HPO_4$ dissolved in 400 mls water. |
| Gentamicin Solution: | 1.9 mls of 50 mg/ml stock diluted with 38 mls water and 0.1 4N NaOH |
| Cycloheximide Solution: | 1.0 mg dissolved in 2 mls of water |

The following reagents are added to a flask containing 400 ml of phosphate buffer (with adjustment in pH after each such addition) to prepare a 500 ml pilot blood gas control. The order of addition of reagents to the buffer is as follows:

Level I Blood Gas Control (no foaming agent)
1. Add 11.5 ml Gentamicin Solution
2. Add 0.5 ml Cycloheximide Solution
3. Adjust pH with HCl to 7.17
4. Add 5 ml $NaHCO_3$ and 0.5 ml HCl pH=7.099, $pCO_2$=31.5
5. Adjust pH with NaOH to 7.215 $pCO_2$=24.8

The contents of flask are now set aside for overnight storage to allow for equilibration of the contents of the solution. The following morning the remaining constituents of the control are added to the flask in the following order:
6. Add 0.1 grams of FDC red dye #40 pH 7.174, $pCO_2$=18.1

The contents of the flask are filtered through a 0.22 micron sterile filter for removal of microbes in other particulates and the fluid, thus, recovered is placed in a sterile, sealed vessel equipped with access means to enable continuous monitoring of pH, and $pCO_2$; and the aseptic addition of the remaining reagents to arrive at the desired assigned values for pH and $pCO_2$.
7. Adjust pH with HCl to 7.121 and $pCO_2$ with $NaHCO_3$ to 31.4
8. Adjust $pCO_2$ with $NaHCO_3$ to 64.1 pH=7.168

Two ml fractions of the solution prepared as described above are placed in sealable glass vials, the head space of each such vial flushed with gas at its assigned values (10% $CO_2$/5% $O_2$/85% $N_2$) and sealed.

Level IA Blood Gas Control (with foaming agent)

A second blood gas control, IA, is prepared in a manner analogous to that described above except for the addition of 30 grams bovine serum albumin (BSA) as foaming agent.

Each control is agitated in its sealed vial for ten (10) seconds, the vials opened and the values of pH, $pCO_2$ and $pO_2$ plotted as a function of time. As is readily apparent, the foam generated in agitation of control IA provides an effective barrier against atmospheric contamination for up to ten (10) minutes in the case of assigned values for pH; ten (10) minutes in the case of the assigned values of $pCO_2$ and ten (10) minutes in the case of the assigned values for $pO_2$. By comparison, the blood gas control deficient in foaming agent, experiences almost an immediate change in assigned values for all three such parameters.

The foregoing description and Example have been provided as illustrative of but some of the preferred embodiments of this invention and not intended as delineation of its scope which is set forth in the following claims.

What is claimed is:

1. A blood gas control for quality control measurement of pH and one or more blood gases comprising: in a sealed receptacle, impermeable to gas exchange with the ambient environment, an aqueous, essentially cell-free, stable blood gas control fluid consisting essentially of having an isolation effective amount of a non-primate proteinaceous foaming agent, an assigned concentration of dissolved carbon dioxide and dissolved oxygen, a buffer, and a gaseous head space, the amount of foaming agent in said fluid being (i) insufficient to adversely effect the shelf life of the control in the sealed receptacle, (ii) capable, upon agitation of the sealed receptacle, of forming a gas impermeable foam barrier which effectively isolates the control fluid from the ambient environment upon opening of said receptacle, and (iii) approximate the concentration of protein in human serum, thereby maintaining, for a finite interval, the level of dissolved gas in said control fluid at essentially its assigned value.

2. The blood gas control of claim 1 wherein the foaming agent comprises bovine serum albumin.

3. The blood gas control of claim 1 further comprising a minor amount of inert detergent.

4. The blood gas control of claim 1 wherein the viscosity of the control is comparable to that of human serum.

5. The blood gas control of claim 1, wherein the gaseous head space comprises nitrogen, oxygen and/or carbon dioxide as essentially the same assigned values as the concentration of nitrogen, oxygen and/or carbon dioxide which is dissolved in said fluid.

6. An essentially cell-free, stable blood gas control fluid consisting essentially of a buffer, an assigned concentration of dissolved carbon dioxide, dissolved oxygen, and an isolation effective amount of a non-primate proteinaceous foaming agent, the concentration of said foaming agent being in the range of from about 5 to about 7 grams perdeciliter so as to approximate the amount of protein present in human blood and the concentration of dissolved carbon dioxide and dissolved oxygen being at levels assigned relative to the function of the control fluid.

7. The control fluid of claim 6, wherein the foaming agent comprises bovine serum albumin.

8. The control fluid of claim 6, further comprising a minor amount of inert detergent.

9. The control fluid of claim 6, wherein the viscosity is comparable to that of human serum.

* * * * *